United States Patent [19]

Haak et al.

[11] Patent Number: 4,927,408
[45] Date of Patent: May 22, 1990

[54] ELECTROTRANSPORT TRANSDERMAL SYSTEM

[75] Inventors: Ronald P. Haak, Cupertino; Felix Theeuwes; J. Richard Gyory, both of Los Altos, all of Calif.

[73] Assignee: Alza Corporation, Palo Alto, Calif.

[21] Appl. No.: 252,463

[22] Filed: Oct. 3, 1988

[51] Int. Cl.⁵ .............................................. A61N 1/30
[52] U.S. Cl. ........................................ 604/20; 128/798
[58] Field of Search .................. 604/20; 128/802, 803, 128/798

[56] References Cited

U.S. PATENT DOCUMENTS

| 4,001,200 | 1/1977 | Bonsen et al. | 260/112.5 R |
|---|---|---|---|
| 4,144,317 | 3/1979 | Higuchi | 424/21 |
| 4,274,420 | 6/1981 | Hymes | 128/641 |
| 4,325,367 | 4/1982 | Tapper | 128/207.21 |
| 4,391,278 | 7/1983 | Cahalan et al. | 128/640 |
| 4,406,658 | 9/1983 | Lattin | 128/802 |
| 4,419,092 | 12/1983 | Jacobsen et al. | 604/20 |
| 4,457,748 | 7/1984 | Lattin et al. | 604/20 |
| 4,474,570 | 10/1984 | Ariura et al. | 604/20 |
| 4,557,723 | 12/1985 | Sibalis | 604/20 |
| 4,622,031 | 11/1986 | Sibalis | 604/20 |
| 4,640,689 | 2/1987 | Sibalis | 604/20 |
| 4,689,039 | 8/1987 | Masaki | 604/20 |
| 4,702,732 | 10/1987 | Powers et al. | 604/20 |
| 4,708,716 | 11/1987 | Sibalis | 604/20 |
| 4,713,050 | 12/1987 | Sibalis | 604/20 |
| 4,722,726 | 2/1988 | Sanderson et al. | 604/20 |
| 4,731,049 | 3/1988 | Parsi | 604/20 |
| 4,731,926 | 3/1988 | Sibalis | 29/877 |
| 4,767,401 | 8/1988 | Seiderman | 128/803 |

FOREIGN PATENT DOCUMENTS 8607269 12/1986 PCT Int'l Appl. ............. 128/419 R
8800846 2/1988 PCT Int'l Appl. ................... 604/20

OTHER PUBLICATIONS

P. Tyle & B. Kari, "Iontophoretic Devices," in Drug Delivery Devices, pp. 421-454 (1988).

Primary Examiner—Lee S. Cohen
Assistant Examiner—Scott Getzow
Attorney, Agent, or Firm—D. Byron Miller; Steven F. Stone; Edward L. Mandell

[57] ABSTRACT

A transdermal therapeutic system which utilizes electrical current to facilitate agent delivery and which isolates the electrochemical reactants and products from the agent containing reservoir.

21 Claims, 3 Drawing Sheets

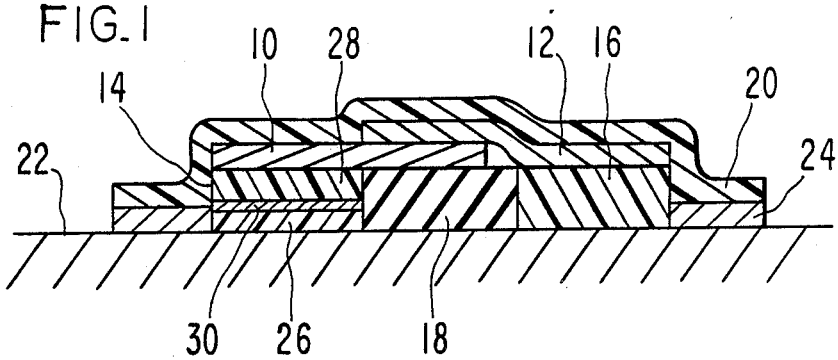
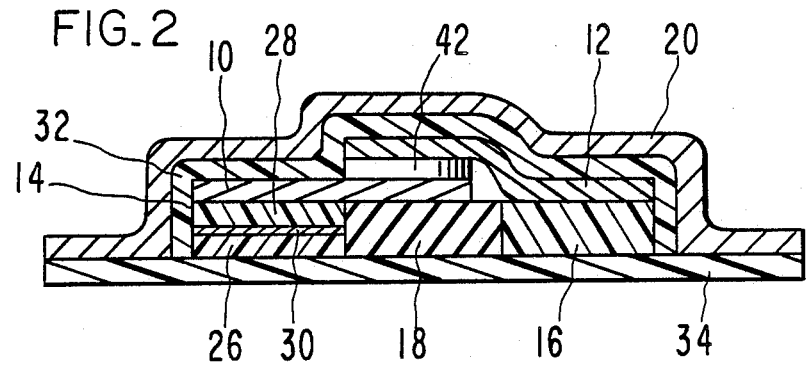
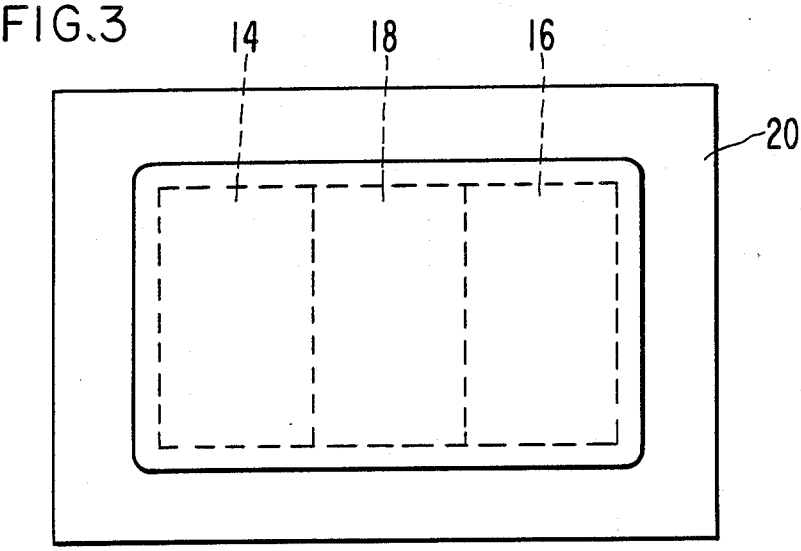

ELECTROTRANSPORT TRANSDERMAL SYSTEM

FIELD OF THE INVENTION

This invention relates to transdermal and transmucosal drug delivery. More particularly, this invention relates to transdermal drug delivery systems capable of delivering drugs or dose regimens not otherwise suitable for passive drug delivery. Still more particularly, but without limitation thereto, this invention relates to transdermal systems which utilize electrical current to facilitate drug delivery.

RELATED PATENT APPLICATIONS

This invention is related to the invention disclosed in the copending, coassigned patent application of Gyory et al entitled "Electrotransport Transdermal System," U.S. Ser. No. 07/215,150, filed on July 5, 1988, which is incorporated herein by reference.

BACKGROUND OF THE INVENTION

Many drugs are not suitable for passive drug delivery because of their size, ionic charge characteristics and hydrophilicity. One method of overcoming this limitation in order to achieve transdermal administration of such drugs is the use of electrical current or an electrical potential gradient to actively transport drugs into the body, as for example, through intact skin or other tissues. This concept is based upon basic principles of electrochemistry and is defined as electrically-assisted transport, hereinafter referred to as "electrotransport". An electrochemical cell in its simplest form consists of two electrodes and associated half cell reactions, between which electrical current can flow. Electrical current flowing through the metal portion of the circuit is carried by electrons (electronic conduction), while current flowing through the liquid phase is carried by ions (ionic conduction). Current flows as an electrical charge is transferred to chemical species in solution by means of oxidation and reduction charge transfer reactions at the electrode surfaces. A detailed description of the electrochemical processes involved in electrically-assisted drug transport can be found in electrochemistry texts such as J. S. Newman, Electrochemical Systems (Prentice Hall, 1973) and A. J. Bard & L. R. Faulkner, Electrochemical Methods, Fundamentals and Applications (John Wiley & Sons, 1980). Therefore, only pertinent portions will be presented here.

As electrical current flows, oxidation and reduction of some chemical species take place. A variety of electrochemical reactions can be utilized, and these fall into two classes. In one class, the electrode material participates in the charge transfer reaction; i.e., the electrode material is consumed or generated. In the other class, the electrode material behaves as a catalyst; i.e., the reduced and oxidized species exist in solution and the charge transfer reaction is catalyzed at the electrode surface. An example of the former is represented by :

$$Zn \rightleftharpoons Zn^{+2} + 2e^-$$

or $$Ag + Cl^- \rightleftharpoons AgCl + e^-$$

where the forward reaction is the oxidation or anodic process and the reverse reaction is the reduction or cathodic process.

Examples of electrochemical reactions involving species independent of the electrode materials are the hydroquinone/quinone and the ferrous/ferric ion couples:

$$H_2Q \rightleftharpoons Q + 2H^+ + 2e^-$$

and $$Fe^{++} \rightleftharpoons Fe^{+++} + 30\ e^-$$

Again, the forward reaction is the anodic process and the reverse reaction is cathodic. These reactions are catalyzed by an appropriate polarized surface.

When electrical charge is either generated or consumed at an electrode surface, ionic species must be transported to maintain electroneutrality throughout the system. Electrically-assisted transport or electrotransport, is defined as the mass transport of a particular chemical species through a biological interface or membrane when an electrical potential gradient is imposed across said interface or membrane Three physical processes contribute to this transport: passive diffusion, electromigration and convection.

In applying these principles to drug delivery, the drug being delivered can be electrically-assisted into the skin. There are a number of categories in which drug delivery systems utilizing electrotransport principles can offer major therapeutic advantages. See P. Tyle & B. Kari, "Iontophoretic Devices", in DRUG DELIVERY DEVICES, pp.421–454 (1988).

Even though the concept of electrotransport in drug delivery is there is a continuing need to develop systems which overcome the problems associated with known electrotransport devices. Typical electrotransport systems combine the agent or drug to be delivered with other electrolyte components such as buffers, salts and electrochemical reactants. In such a system, these species could either react directly with the drug or change the composition of the drug reservoir such that the performance of the delivery system is adversely affected. For example, a reaction product capable of causing precipitation of the drug which subsequently blocks and insulates the electrode surface would be a detriment to the overall system and process. Changes in electrolyte pH can yield drastic changes in transport characteristics and, at some pH values, damage to the skin could occur. Damage to the skin can also occur due to contact with metal ions produced during discharge of the electrodes. In addition, control of the ionic strength of the donor electrolyte can also be very important. This invention addresses the problem by separating the electrolyte from the drug by means of a selectively permeable membrane.

SUMMARY OF THE INVENTION

An object of this invention is to provide an improved approach and device for the controlled and sustained transdermal transport of drugs.

Another object of this invention is to provide for electrically-assisted transdermal delivery of drugs, and also to provide for enhanced drug transport at rates higher than those achieved by passive diffusion.

A further object of this invention is to optimize system components and processes including electrochemical reactions and electrolyte compositions to minimize the electrical power requirement.

A still further object of this invention is to design an electrotransport transdermal drug delivery system where the electrochemical reactants and products are isolated from the drug containing reservoir.

Another object of this invention is to provide programmable drug delivery.

An even further object of this invention is to provide electrically-assisted delivery systems capable of delivering macromolecules such as peptides and polypeptides.

These and other objects, features and advantages of the invention have been demonstrated by the present invention wherein a self contained electrotransport transdermal system for placement on a body surface is comprised of: a non-conductive backing member; a source of electrical power comprising first and second current conducting members, said current conducting members being positioned adjacent to said backing member and either in direct contact with each other so as to form a galvanic couple or positioned in direct contact with opposite poles of a power supply such as a battery; a first electrode pad comprising an electrolyte reservoir and an agent reservoir separated by a selectively permeable membrane, said electrolyte reservoir positioned adjacent to said first current conducting member, and said first electrode pad positioned in current conducting relationship to said body surface; a second electrode pad positioned on the body in relationship to said second current conducting member and positioned in current conducting relationship to said body surface; an optional insulating means, insulating said first and said second electrode pads from each other; and a means for maintaining said system in current conducting and agent transmitting relationship to said body surface.

BRIEF DESCRIPTION OF THE DRAWING

The invention will be described in further detail with reference to the accompanying drawings wherein:

FIG. 1 is a schematic cross sectional view of one embodiment of the electrotransport transdermal therapeutic system of this invention having a peripheral adhesive layer, where electrical power is supplied by a galvanic couple;

FIG. 2 is a schematic cross sectional view of an embodiment of this invention having an adhesive overlay and an integral power source;

FIG. 3 is a top view of the embodiments of FIGS. 1 and 2;

DESCRIPTION OF THE INVENTION

Figure 4:
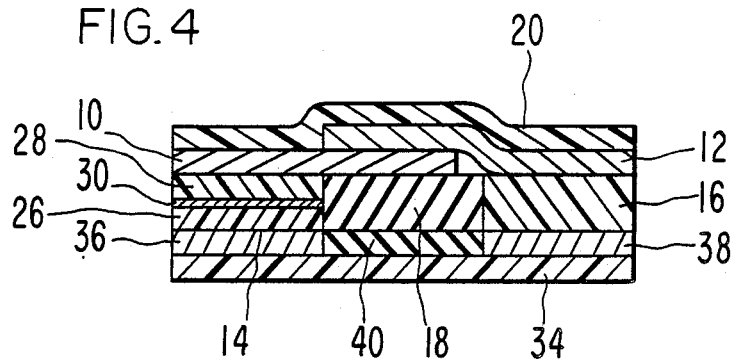
FIG. 4 is a schematic cross sectional view of an embodiment of the invention having an in-line ion conducting contact adhesive.

It is believed that this invention has utility in connection with the delivery of drugs within the broad class normally delivered through body surfaces and membranes, including skin, mucosa and nails. As used herein, the expressions "agent" and "drug" are used interchangeable and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugsm, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

More specifically, it is anticipated that this invention will prove to be useful in the controlled delivery of metoclopramide, baclofen, betamethasone, beclomethasone, doxazosin, droperidol, fentanyl, sufentanil, leuprolide (LHRH), lidocaine, methotrexate, micanazole, prazosin, piroxicam, verapamil, tetracaine, diltiazam, indomethacin, hydrocortisone, terbutaline and encainide. It is preferable to use the most water soluble form of the drug or agent to be delivered, which in most instances is the salt form of said drug or agent.

This invention is best described with reference to the accompanying drawings. In general terms, this invention, of which FIG. 1 is a typical example, is an electrotransport transdermal system having two current conducting members, referred to herein as a donor electrode 10 and a counter electrode 12, each electrode being positioned adjacent to the donor electrode pad 14 and counter electrode pad 16, respectively. The pads are separated by an insulator 18. The system has a backing layer 20 made of an electrically insulating or non-conductive material such as is commonly used in transdermal systems. The system adheres to the skin 22 by means of a peripheral adhesive layer 24. Suitable adhesives include, without limitation, polyisobutylene/mineral oil and silicone adhesives. The system would normally include a strippable release liner, not shown. This invention is directed to a novel donor electrode pad 14 which is comprised of an agent reservoir 26 and an electrolyte reservoir 28, separated by a selectively permeable membrane 30.

The selectively permeable membrane material can be chosen to suit the particular needs of the system and will depend upon the composition of the electrolyte reservoir 28, i.e., electrochemical reactants and products, the transference of current out of the reservoir, and the desired selectivity to transport of particular types of charged and uncharged species. A microporous polymer such as is known in the art, can be utilized if the electrolyte reservoir and drug reservoir components can be separated on the basis of size. Therefore, selectively permeable membrane 30 comprised of a microporous polymer can be used to exclude transport of compounds having greater than a predetermined molecule weight. Suitable materials include, without limitation, polycarbonates i.e., linear polyesters of carbonic acids in which carbonate groups recur in the polymer chain by phosgenation of a dihydroxy aromatic such as bisphenol A, polyvinylchlorides, polyamides such as polyhexamethylene adipamide and other such polyamides commonly known as "nylon", modacrylic copolymers such as those formed of polyvinylchloride and acrylonitrile, and styrene-acrylic acid copolymers, polysulfones such as those characterized by diphenylene sulfone groups in the linear chain thereof, halogenated polymers such as polyvinylidene fluoride and polyvinylfluoride, polychloroethers and thermoplastic polyethers, acetal polymers such as polyformaldehyde, acrylic resins such as polyacrylonitrile, polymethyl methacrylate and poly n-butyl methacrylate, polyurethanes, polyimides, polybenzimidazoles, polyvinyl acetate, aromatic and aliphatic polyethers, cellulose esters such as cellulose triacetate, cellulose, collodion, epoxy resins, olefins such as polyethylene and polypropylene, porous rubber, cross-linked poly-(ethylene oxide), cross-linked polyvinylpyrrolidone, cross-linked poly(vinyl alcohol); derivatives of polystyrene such as poly (sodium styrenesulfonate) and polyvinylbenzyltrimethyl-ammonium chloride, poly(hydroxyethyl methacrylate), poly(isobutyl vinyl ether), polyisoprenes, polyalkenes, ethylene vinyl acetate copolymers such as those described in U.S. Pat. No. 4,144,317, incorporated herein by reference, polyamides, polyurethanes, polyethylene oxides, polyox, polyox blended with polyacrylic acid or Carbopol ®, cellulose derivatives such as hydroxypropyl methyl cellulose, hydroxyethyl cellulose, hydroxypropyl cellulose, pectin, starch, guar gum, locust bean gum, and the like, along with blends thereof. This list is merely exemplary of the materials suited for use in this invention. A more extensive list can be found in J. R. Scott & W. J. Roff, Handbook of Common Polymers (CRC Press, 1971) and in patents disclosing suitable materials for use in manufacturing microporous membranes such as U.S. Pat. No. 3,797,494, incorporated herein by reference.

An ion-exchange membrane such as is known in the art, can be utilized as the selectively permeable membrane 30, if the electrolyte reservoir and drug reservoir components can be separated on the basis of their charge characteristics. Therefore, selectively permeable membrane 30 comprised of an ion exchange membrane could be used to inhibit transport of species having a given ionic charge. Suitable ion-exchange membranes include anionic and cationic membranes sold under the trademark Raipore ®, by The Electrosynthesis Co., East Amherst, N.Y. These can provide ion-exchange capacities within the range of 0.8-1.5 meq/g and resistances within the range of 0.2-17 ohm cm$^2$ (measured in 0.6N KCl). These include Raipore cation-exchange membranes 1010, 4010 and 5010 and anion-exchange membranes 1030, 4030 and 5030. Other suitable ion-exchange membranes include, without limitation, ESC-7000 and ESC-7001 and Sybron membranes Ionac MC-3470 and MA-3475.

The ion-exchange membrane may be used to control the movement of ionic species by only allowing species of a specific ionic charge to pass through and may be either of the same or opposite charge than the agent or drug to be delivered. For example, for a positive drug, an anion-exchange membrane will inhibit the drug from moving into the electrolyte reservoir and will inhibit positive ions in the electrolyte reservoir from moving into the agent or drug reservoir where they would compete with the drug for charge transference. However, if the object is to prevent a negatively charged species in the electrolyte reservoir from entering the drug reservoir and causing precipitation of the drug, it would be advantageous to use a cation-exchange membrane in order to prevent this movement.

An ion-exchange membrane can also be used to specifically bind an interfering species and replace it with another. For example, a chelating membrane will effectively remove all metals, especially divalent ones, from solution. Also, a sodium loaded film may be used to replace hydrogen ions. Note that it is important that the membrane have enough capacity to last for the duration of the treatment. For an electrotransport system operating for a 24 hour period at a current of 0.1 mA, the ion-exchange capacity needed will be approximately $9 \times 10^{-5}$ equivalents. Typical commercially available ion exchange membranes are 0.1-0.5 mm thick and are on the order of $10^{-3}$ eq/cm$^3$. These factors should be taken into consideration when selecting a suitable membrane.

The selectively permeable membrane 30 may also be a hydrogel, optionally partially cross-linked, and loaded with a chelating agent to trap the metal ions produced during the discharge of the electrode. This is particularly desirable when the metal ions may damage the skin or body surface. Use of a hydrogel/chelating agent membrane is therefore ionically selective in trapping the metal ions while allowing passage of the counter ions. The hydrogel can be any state of the art material including, without limitation, polyvinylalcohol, polyacrylamide, hydroxypropylmethyl cellulose, hydroxyethylcellulose, hydroxymethylcellulose, polyacrylic acid, polyvinylpyrrolidone, hydroxyethylmethacrylate, albumin, gelatin and cellulose. Suitable chelating agents include, without limitation, ethylenediaminetetraacetic acid (EDTA) and ion-exchange resins such as Chelex 100. Other suitable chelating agents are discussed at length in Martin, Swarbrick and Cammarata, Physical Pharmacy, 3rd edition (1983). Also suitable for use as a material for membrane 30 is a cross-linked polyhemoglobin, such as is described in U.S. Pat. No. 4,001,200, incorporated herein by reference. Cross-linked polyhemoglobin by itself can perform the functions of both the hydrogel and the chelating agent.

The size of the electrotransport transdermal system of this invention can vary from less than 1 cm$^2$ to greater than 200 cm$^2$. The average system however, will have a size within the range of about 5-50 cm$^2$.

FIG. 2 is an embodiment illustrating use of an adhesive overlay 32. This is advantageous when the ions flowing out of or into the electrode pads may be incompatible with the adhesive material The system is also illustrated with a strippable release liner 34.

FIGS. 1 and 2 illustrate parallel alignment of the counter and donor electrodes and pads, as is shown by the top view in FIG. 3.

FIG. 4 is another embodiment of the invention, where the adhesive is positioned between the skin and the electrode pads 14 and 16. In order to allow the system to transfer components to and from the skin, the adhesive must be ion conducting. To avoid transference of ions along the skin surface, the adhesive 36 under the donor electrode pad 14 is separated from the adhesive 38 under the counter electrode pad 16 by a barrier 40, such as an air gap, a non-ion conducting hydrophobic adhesive or other suitable barrier to ion flow.

Figure 5:
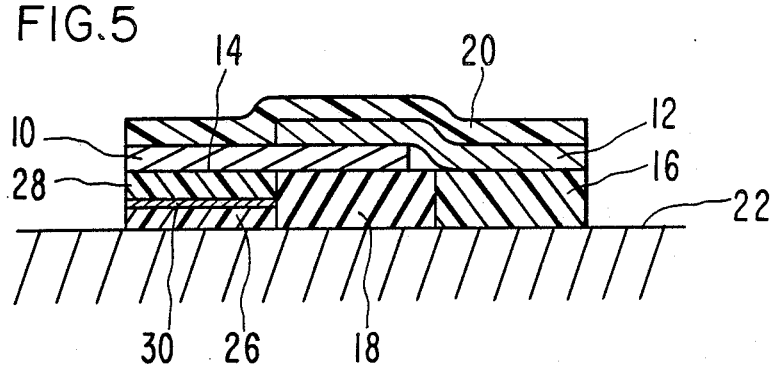
FIG. 5 is a schematic cross sectional view of an embodiment of the invention having a self-adhering matrix.
Figure 6:
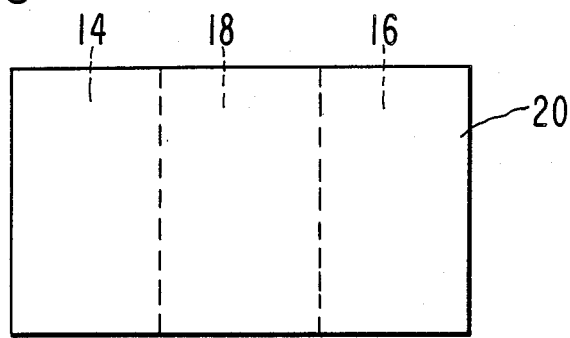
FIG. 6 is a top view of the embodiments of FIGS. 4 and 5.

FIG. 5 illustrates a system where the agent reservoir 26 and the counter electrode pad 16 are self-adhering matrices. FIG. 6 provides a top view which illustrates that this embodiment provides for parallel alignment of the donor and counter electrode pads.

Figure 7:
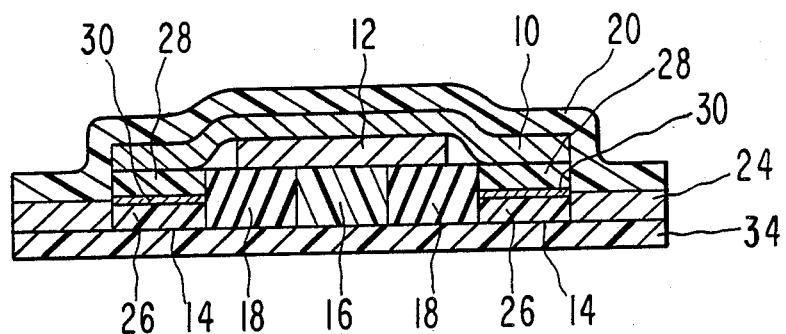
FIG. 7 is a schematic cross sectional view of another embodiment of this invention where the donor electrode is surrounded at its periphery by the counter electrode.
Figure 8:
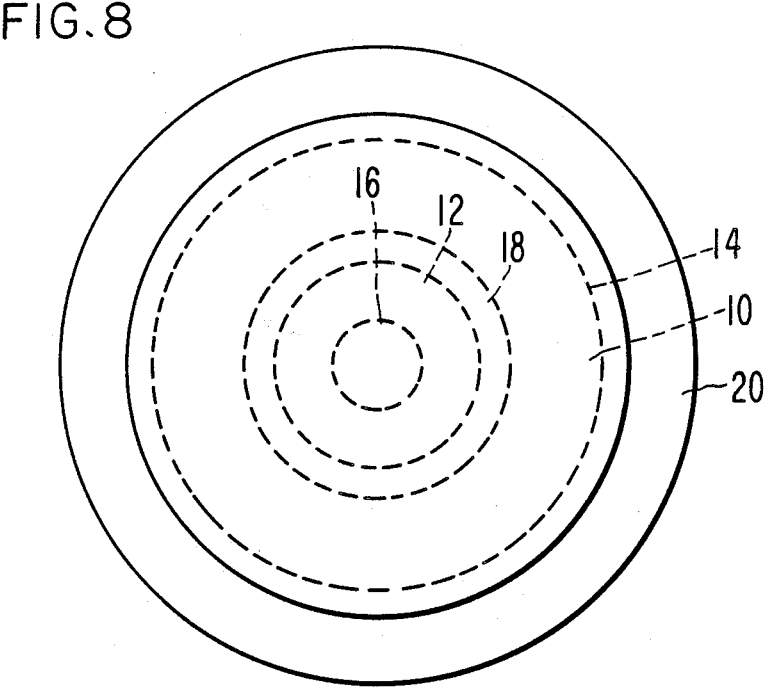
FIG. 8 is a top view of the embodiment of FIG. 7.

In an alternate design, the electrodes can be aligned peripherally. This is shown in FIG. 7 where the counter electrode pad 16 is in the center, surrounded by an insulator 18 and the donor electrode pad 14. The electrode pads can also be reversed with the counter electrode pad on the exterior and the donor electrode pad in the center, if desired. The peripheral alignment can be circular as is shown by the top view in FIG. 8. However, this invention is not limited to that configuration and can be, for example, elliptical, rectangular or any of a variety of geometric configurations.

Transport of species during the passage of electrical current is accomplished via the following mechanisms: passive diffusion, electromigration and electroosmosis. The latter two electrokinetic processes are of the greatest concern, since the object of this invention is to use electrical current to enhance the transdermal transport obtained by passive diffusion alone. For purposes of illustration only, the drug being delivered shall be referred to as being positively charged. It is to be understood however, that both negatively charged and neutral drug molecules can also be delivered by the electrotransport systems of this invention.

Further, for illustration purposes only, the donor electrode pad 14 shall be described as containing the drug to be delivered and the counter electrode pad 16 shall be described as containing a cation-anion pair. This invention does however, contemplate placing drug in both electrode pads and in that manner both pads would function as donor electrode pads and would each have electrolyte reservoirs separated from their respective drug reservoirs by selectively permeable membranes. For example, positive ions could be introduced into tissues from the anode (positive electrode), while negative ions could be introduced from the cathode (negative pole). Alternatively, neutral drugs can be introduced from either electrode by electroosmosis.

The embodiment of FIG. 1 is a galvanic couple formed by the donor 10 and counter 12 electrodes, which for a positively charged drug are the anode and cathode, respectively. When the system is in storage no current flows because the circuit is not closed. The circuit is closed when the system is placed on the skin 22, the body acting as an ion-conducting pathway, as is shown in FIG. 1.

Power Supply

The electrotransport transdermal system of this invention can operate in numerous ways, depending upon the requirements of the system.

If the counter and donor electrodes are of dissimilar metals or have different half cell reactions, it is possible for the system to generate its own electrical power. This embodiment is shown in FIG. 1 where the electrodes 10 and 12 are positioned adjacent to each other and to their respective electrode pads. Typical materials to provide such a galvanic couple include using a zinc donor electrode 10 and a silver/silver chloride counter electrode 12. Such a combination can provide about 1 volt.

In this instance, the donor electrode pad 14 is an integral part of the power generating process. The system activates automatically when applied to intact skin because at that time the electrical conduction circuit is closed and drug transport is initiated.

In some instances it may be necessary to augment the power supplied by the galvanic electrode couple. This can be accomplished by placement of a separate power source 42, such as a battery or series of batteries, positioned between the donor electrode 10 and the counter electrode 12 as is shown in FIG. 2, such that electrode 10 is in direct contact with one pole of the power supply and electrode 12 is in direct contact with the opposite pole. The selection of electrochemical reactions for use in electrotransport systems are governed by various considerations including: the thermodynamics and kinetics of the reactions; the effect the reactants and products have on the electrolyte compositions, for example, the pH and ionic strength; the compatibility of the electrode materials, reactants and products with other cell components, for example, the drug species; and the biocompatibility of the reactants and the products.

Standard electrochemical reactions and the respective reduction potentials are well known in the art. See the CRC Handbook of Chemistry and Physics, pp. D 151-158, 67th edition (1986-1987). Proper selection of the components and electrochemical reactions for the anode and cathode can allow the transdermal electrotransport system to function as its own battery. For example, use of the following reaction at the anode:

$$Zn \longrightarrow Zn^{+2} + 2e^- \quad E_{oxidation} = 0.763 \text{ volts}$$

and the following reaction at the cathode:

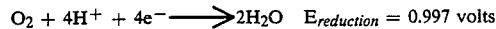

$$O_2 + 4H^+ + 4e^- \longrightarrow 2H_2O \quad E_{reduction} = 0.997 \text{ volts}$$

a cell voltage of about 1.76 volts (0.763+0.997) at a pH of 4, can be obtained. If the average skin resistance is about 10 kohms-cm$^2$ (R) and the skin resistance is the predominant impedance component, then a current of about 85 $\mu$A/cm$^2$ could be achieved without the use of an external power supply. This is based on the resistance of two skin layers and it is assumed that there is negligible resistance within the donor and counter electrode pads.

This is all based upon Ohm's Law which states that:

$$V = (I)(R)$$

where
 V = voltage
 I = current
 R = resistance

The resistance as noted above, is primarily that of the skin. A desired current density is established and from those values, the voltage requirements of the system can be determined.

In addition to the thermodynamics of the electrochemical reactions, the kinetics of the processes must be considered. The primary concern is that the reaction can proceed at a rate sufficient to maintain the desired current. If the reaction kinetics are too slow, other reactions will occur and could introduce contaminants which are detrimental to the overall electrotransport process, for example by changing the pH of the electrolyte. One measure of the kinetics of a reaction is the reversibility of the reaction. For the present applications, it is important to insure that the kinetics of a reaction in one direction (oxidation at the anode, reduction at the cathode) are adequate for the desired system discharge rates.

This invention also contemplates those situations where the electrochemical reactions are not sufficient to drive the system and the system is supplemented with an integral power source 42 positioned between the donor electrode 10 and the counter electrode 12, as is shown in FIG. 2. An example of a suitable power source is one or more batteries in series, such as 3 volt lithium batteries. By utilizing an independent power source, the electrodes can be similar metals.

A constant current insures a constant ion flow across the skin, regardless of fluctuations in the impedances associated with other system components. The current level can be controlled by a variety of means. For example, a resistor, in series with the electrotransport cell and battery, having a resistance substantially greater than the overall cell resistance could limit the current to some level, although at the expense of consuming a large portion of the battery's power. The ideal controller would not consume much voltage or power. A much better current source can be made by the use of an appropriate field effect transistor (FET) circuit. FET current controllers which consume only about 0.5–0.7 volts are commercially available.

While the above describes some very simple approaches to electrical power supply and control for electrotransport systems, clearly the list of more complex systems is essentially endless. For example, controllers could be designed which permit the patient to turn the electrotransport system on and off such as with an on-demand medication regimen, or to turn the system on and off at some desired periodicity to match the natural or circadian patterns of the body. A relatively simple controller or microprocessor could control the current as a function of time or could generate complex current waveforms such as pulses or sinusoidal waves. Ultimately, controllers might employ some type of feedback system which would monitor biosignals, provide an assessment of the therapy, and adjust the drug delivery accordingly. A typical example, is the monitoring of the blood sugar level for controlled administration of insulin.

Electrode Pads

The agent reservoir 26 and electrolyte reservoir 28 of the donor electrode pad 14, along with the counter electrode pad 16 can be a polymeric matrix structure formed by blending the desired agent, drug, electrolyte or other component(s), with an inert polymer by melt blending or solvent casting or extrusion, for example. The components are preferentially present in a ratio of total blend of about 25 to 90 percent to insure an open pore (microporous) structure in the polymer. For the drug reservoir 26, lower component (drug) concentrations may be useful if a delay in release from the system is desired. The electrolyte reservoir 28 and the counter electrode pad 16 may contain any one or more of the following: NaCl, electrochemically inert salts and buffers, and electrolytes containing redox species such as $Cu^{=2}$, $Fe^{=2}$, $Fe^{=3}$, quinone, hydroquinone, $Ag^{=}$ and $IO_3^{-}$.

Suitable polymers are those which can be blended with the components in the melt phase. These include, without limitation, polyethylene, polypropylene, polyisoprenes and polyalkenes, polyvinylacetate, ethylene vinyl acetate polymers such as those described in U.S. Pat. No. 4,144,317, incorporated herein by reference, polyamides and polyurethanes. The matrix can also be prepared to include plasticizers in polymers such as polyvinylchloride, cellulose acetate and cellulose acetate butyrate, and blends thereof.

Other suitable polymers are those which dissolve in organic solvents. These include, without limitation, ethylcellulose, cellulose acetate, ethylene vinyl acetate, polyurethane and nylons, and blends thereof.

The matrix can be crosslinked with the components in place such as a silastic matrix, or the polymers can be prefabricated and sorbed with the components from solutions as is the case with cellulose, woven fiber pads and sponges. The reservoirs 26 and 28 and pad 16 can alternately be a gel matrix structure, formed similarly to the polymeric matrix structure wherein the gel is formed of a hydrophilic polymer which is swellable or soluble in water. Such polymers can be blended with the components in any ratio, preferably from a few percent up to 50 percent. The polymers can be linear or cross-linked and suitable examples include, without limitation, polyethylene oxides, polyox, polyox blended with polyacrylic acid or Carbopol ®, cellulose derivatives such as hydroxypropyl methyl cellulose, hydroxyethyl cellulose, hydroxypropyl cellulose, pectin, starch, guar gum, locust bean gum, and the like, along with blends thereof. This list is merely exemplary of the materials suited for use in this invention. A more extensive list can be found in J. R. Scott & W. J. Roff, Handbook of Common Polymers (CRC Press, 1971).

Supporting electrolytes which are chemically inert and pharmacologically nontoxic, may also be included in both the reservoirs and in the counter electrode pad. The drug itself often acts as a buffer and so the addition of buffers is often not necessary.

FIGS. 1, 2, 4 and 7 illustrate embodiments of the invention which adhere by means of in-line ion conducting adhesive, a peripheral adhesive or an adhesive overlay. Use of a separate adhesive can be eliminated entirely by selecting a material such that agent reservoir 26 and pad 16 are self-adhering matrices, as is shown in FIG. 5. Suitable self-adhering matrix materials include, without limitation, poly(styrenebutadiene) and poly(styrene-isoprene-styrene) block copolymers, and a high and low molecular weight polyisobutylene copolymers. Other suitable self-adhering matrix materials are set forth in the art such as are described in U.S. Pat. Nos. 4,391,278, 4,474,570, and 4,702,732, all of which are incorporated herein by reference.

The matrix may also be of an ethylene vinyl acetate (EVA) copolymer of the type described above. Adhesive properties are preferably enhanced by adding a resinous tackifier. this is especially important when using a non-tacky polymeric matrix. Example of suitable tackifiers include products sold under the trademarks Staybelite Ester #5 and #10, Regal-Rez and Piccotac, all of Hercules, New Jersey. Additionally, the matrix may contain a rheological agent, suitable examples of which include mineral oil and silica.

The agent reservoir 26 can also be an ion-exchange structure. The rationale for choosing the polymeric counter-ion to the drug is to the counter-ion. The ion exchange structure can be an ion-exchange membrane which is prepared from a prefabricated membrane having the desired ion-exchange capacity and conductance. The agent reservoir 26 is loaded with drug by soaking the ion-exchange membrane in a drug solution at a pH where the drug is ionized as well as the resin. Suitable materials for use with this invention are anionic and cationic membranes such as those described herein with reference to the selectively permeable membrane 30.

Alternately, the ion-exchange structure can be a heterogeneous matrix. Agent reservoir 26 can be fabricated by loading ion-exchange resin beads with drug by soaking, as described above. The resin beads can subsequently be compounded into a matrix structure by melt blending the beads with molten polymer matrix and subsequent extrusion. Suitable polymers are those with sufficiently low melting points and include, without limitation, polyethylene, polyalkenes, rubbers, copolymers such as Kraton ®, ethylene vinyl acetate, nylons and polyurethanes. The agent reservoir 26 can also be loading the ion-exchange beads (containing drug) into a matrix that is subsequently cross-linked, similar to silicone rubber. Alternately, the beads can be blended in an organic solvent containing a polymeric binder such as ethylcellulose dissolved in methylene chloride or methanol, or cellulose acetate, polyurethane or rubber dissolved in petroleum ether. Generally, suitable binder polymers are selected from materials having low electrical or ion conductive properties.

Suitable commercially available cation and anion resins include, without limitation, those listed below.

TABLE I

| NAME (BACKBONE) | FORM | SIZE mesh | DRY meq/g | RESIN BED meq/ml | MOISTURE % of total | PORE SIZE |
|---|---|---|---|---|---|---|
| Cation-Exchange Resins | | | | | | |
| AG 50W-X12* (Sulfonic acid) | H | 100–200 | 5 | 2.3 | 42–48 | small |
| Bio-Rex 70* (Carboxylic acid) | Na | 200–400 | 10.2 | 3.3 | 65–74 | large |
| Chelex 100* Chelating resin (Iminodiacetic acid) | Na | 100–200 | 2.9 | 0.7 | 71–76 | large |
| Amberlite IR-120** (Sulfonic acid) | H | 20–50 | 5.0 | 1.8 | 49–55 | medium |
| Anion-Exchange Resins | | | | | | |
| AG 1-X8* ($R_4N^+$) | Cl | 20–50 | 3.2 | 1.4 | 39–45 | medium |
| Amberlite IRA-400** ($RN(CH_3)_3^+$) | Cl | 20–50 | 3.3 | 1.2 | 42–48 | medium |

*represents Trademark names of Bio-Rad
**represents Trademark names of Mallinckrodt In general, the counter electrode pad 16 will contain an appropriate amount of a suitable redox species and a relatively high concentration of a chemically inert, pharmacologically non-toxic salt such as sodium chloride, alkaline salts, chlorides, sulfates, nitrates, carbonates, phosphates, and organic salts such as ascorbates, citrates, acetates and mixtures thereof. The addition of a buffer is also usually desired. An example of a suitable counter electrode pad composition when the counter electrode is a silver/silver chloride cathode, is an electrolyte containing sodium chloride with a sodium phosphate buffer.

In addition to the agent, drug or electrolyte, the reservoirs and counter electrode pad may also contain other materials such as dyes pigments, inert fillers, excipients, and other conventional components of pharmaceutical products or transdermal therapeutic systems known to the art.

Electrodes

The electrode material is selected based upon the electrochemical considerations enumerated above. Numerous electrode configurations are well known in the art; for example, U.S. Pat. Nos. 4,474,570 and 4,557,723, both of which are incorporated herein by reference. This invention provides a unique configuration whereby the electrodes are in direct contact with each other as in FIG. 1, or with a power source as in FIG. 2. This direct configuration provides a distinct advantage in manufacturing.

Electrodes 10 and 12 can be metal foils. Alternately, the electrodes can be fabricated by calendering, film evaporation or by embedding the metal powder desired in a binder matrix. For example, zinc powder, silver powder and/or silver chloride powder can be embedded in an ethylene vinylacetate matrix, with the preferred amount of metal being within the range of 30–90 volume percent and the remainder being the binder matrix.

Insulator

The insulator 18 performs the function of preventing ion transport between the electrode pads 14 and 16. It is preferably formed of a non-conducting polymeric material, which is impermeable to both the passage of ions and water. One such suitable material is ethylene vinyl acetate, as is described in detail above. Preferably, the insulating material used, will be the same as the polymer selected for the electrode pads to improve bonding between the different system components.

Backing

The non-conducting backing member 20 serves several functions. It protects the electrodes 10 and 12 from exposure. It prevents leakage of drug or other system components. It also can provide support for the system, where needed. Backing member 20 can be flexible or nonflexible and suitable materials include, without limitation, cellophane, cellulose acetate, ethylcellulose, plasticized vinyl acetate-vinyl chloride copolymers, polyethylene terephthalate, polyethylene terephthalate/ethylene vinyl acetate, nylon, high and low density polyethylene, polypropylene, polyester, polycarbonate, polyurethane or other polyester films, polyvinylidene chloride and coated flexible fibrous backings such as paper and cloth. Such backings can be in the form of precast films or fabrics which are bonded to the electrodes by heat or adhesives or they can be coated onto the electrode.

Having thus generally described our invention, the following examples will illustrate how variations of the above described parameters provide therapeutically effective electrotransport systems.

EXAMPLE I

One embodiment of an electrotransport transdermal system according to this invention would have the configuration illustrated in FIG. 1 and would be made of the following materials. The agent reservoir 26 would be 50 dry weight percent EVA 40 and 50 wt. % metoclopramide HCl. The electrolyte reservoir 28 would be 50 dry weight percent EVA 40 and 50 wt. % NaCl and sodium phosphate buffer. The selectively permeable membrane 30 would be a Raipore 4030 anion-exchange membrane. The counter electrode pad 16 would be 50 dry weight percent EVA 40 with the balance being NaCl and sodium phosphate. To form a galvanic couple capable of supplying enough power to run the system, the donor electrode 10 would be Zn while the counter electrode 12 would be Ag/AgCl. Insulator 18 would be EVA 40 backing member 20 would be polyethylene terephthalate/EVA. The system would remain in position by peripheral adhesive 24 made of polyisobutylene and mineral oil. Further, a small amount of tackifier may be added to the EVA 40 reservoirs 26 and 28 to increase the tackiness and therefore insure good contact for the entire system.

EXAMPLE II

Another embodiment of an electrotransparent transdermal system according to this invention would have the configuration illustrated in FIG. 2 and would be made of the following materials. The donor electrode pad 14 and counter electrode pad 16 would have the same composition as that in Example I. The donor electrode 10 would be Ag while the counter electrode 12 would be Ag/AgCl, and positioned between them would be a 3 volt lithium battery acting as the power source 42. Insulator 18 and backing member 20 would be of the same materials as in Example I. The system would remain in position by an adhesive overlay 32 made of polyisobutylene and mineral oil.

EXAMPLE III

Another embodiment of an electrotransport transdermal system according to this invention would have the configuration similar to that illustrated in FIG. 5, the difference being that both electrode pads would deliver drug and therefore both pads would have separate reservoirs for the electrolyte and the drug. Such a system and would be made of the following materials. One agent reservoir would be a self-adhering karaya gum composition containing l-dopa formulated at a pH about 3.5 below the isoelectric point. The other agent reservoir would also be a self-adhering karaya gum composition containing l-dopa formulated at a pH of about 7.5 above the isoelectric point. In this manner, both electrode pads act as donors and deliver agent to the body surface. To form a galvanic couple capable of supplying enough power to run the system, the donor electrode would be Zn while the counter electrode would be Ag/AgCl. The insulator would be EVA 40 and the backing member would be polyethylene terephthalate/EVA.

Having thus generally described our invention and described in detail certain preferred embodiments thereof, it will be readily apparent that various modifications to the invention may be made by workers skilled in the art without departing from the scope of this invention and which is limited only by the following claims.

What is claimed is:

1. An electrotransport system for placement on a body surface and delivering an agent through said surface, the system comprising:
   a non-conductive backing member;
   a source of electrical power comprising first and second current conducting members, said current conducting members being positioned adjacent to said backing member;
   a first electrode pad comprising a first reservoir containing an electrolyte and a second reservoir containing the agent, said electrolyte-containing reservoir, positioned adjacent to said first current conducting member and said agent-containing reservoir adapted to be positioned in current conducting relationship to said body surface;
   a selectively permeable membrane separating the first and second reservoirs from one another, the membrane comprising a microporous polymer which is impermeable to the agent and to chemical species having a molecular weight greater than a predetermined molecular weight and permeable to chemical species having a molecular weight less than the predetermined molecular weight;
   a second electrode pad positioned adjacent to said second current conducting member and adapted to be positioned in current conducting relationship to said body surface;
   an insulating means electrically insulating said first and said second electrode pads from each other; and
   a means for maintaining said system in current conducting and agent transmitting relationship to said body surface.

2. A self contained electrotransport transdermal system for placement on a body surface and delivering an agent through said surface, the system comprising:
   a non-conductive backing member;
   a source of electrical power comprising first and second current conducting members, said current conducting members being positioned adjacent to said backing member, said first current conducting member being composed at least in part of an oxidizable metal;
   a first electrode pad comprising a first reservoir containing an electrolyte and a second reservoir containing the agent, said electrolyte-containing reservoir positioned adjacent to said first current conducting member and said agent-containing reservoir adapted to be positioned in current conducting relationship to said body surface;
   a selectively permeable membrane separating the first and second reservoirs from one another, the membrane comprising a hydrogel material which is loaded with a chelating agent, the loaded hydrogel material being capable of trapping metal ions produced by the oxidation of the metal in the first current conducting member;
   a second electrode pad positioned adjacent to said second current conducting member and adapted to be positioned in current conducting relationship to said body surface;

an insulating means electrically insulating said first and said second electrode pads from each other; and a means for maintaining said system in current conducting and agent transmitting relationship to said body surface.

3. The system of claim 1 or 2, wherein said second electrode pad contains an agent to be delivered.

4. The system of claim 1 or 2, wherein said means for maintaining said system in current conducting and agent transmitting relationship to said body surface is a peripheral adhesive.

5. The system of claim 1 or 2, wherein said means for maintaining said system in current conducting and agent transmitting relationship to said body surface is an adhesive overlay.

6. The system of claim 1 or 2, wherein said means for maintaining said system in current conducting and agent transmitting relationship to said body surface is an in-line ion conducting adhesive positioned between said electrode pads and said body surface.

7. The system of claim 1 or 2, wherein said means for maintaining said system in current conducting and agent transmitting relationship to said body surface comprises utilizing a self-adhering matrix composition for said agent-containing reservoir of said first electrode pad, and said second electrode pad.

8. The system of claim 1 or 2, wherein said first electrode pad, said insulating means and said second electrode pad are aligned in parallel.

9. The system of claim 1 or 2, wherein said first electrode pad, said insulating means and said second electrode pad are peripherally aligned.

10. The system of claim 1 or 2, wherein said agent is a macromolecule.

11. The system of claim 1 or 2, wherein said agent is selected from the group consisting of peptides and polypeptides.

12. The system of claim 1 or 2, wherein said agent is selected from the group consisting of metoclopramide, baclofen, betamethasone, beclomethasone, doxazosin, droperidol, fentanyl, sufentanil, leuprolide, lidocaine, methotrexate, micanazole, prazosin, piroxicam, verapamil, tetracaine, diltiazam, indomethacin, hydrocortisone, terbutaline and encainide.

13. The system of claim 1 or 2, wherein said source of electrical power includes a battery.

14. The system of claim 1 or 2, wherein said source of electrical power includes a galvanic couple formed by the first and second current conducting members contacting one another, said first and second current conducting members being formed of different metals.

15. The system of claim 1 or 2, wherein said source of electrical power produces a constant current.

16. The system of claim 1 or 2, wherein said source of electrical power is controlled by a patient.

17. The system of claim 1 or 2, which further comprises a microprocessor for controlling current produced by the source of electrical power as a function of time.

18. The system of claim 1 or 2, having a feedback system including a sensor for monitoring a biosignal and means for controlling current produced by the electrical power source in response thereto.

19. The system of claim 2, wherein the hydrogel material is partially cross-linked.

20. The system of claim 2, wherein the hydrogel material is selected from the group consisting of polyvinyl alcohol, polyacrylamide, hydroxypropyl methylcellulose, hydroxyethyl cellulose, hydroxymethyl cellulose, polyacrylic acid, polyvinyl pyrrolidone, hydroxyethyl methacrylate, albumin, gelatin and cellulose.

21. The system of claim 2, wherein the chelating agent comprises EDTA.

* * * * *